United States Patent [19]

Lieberman et al.

[11] Patent Number: 4,780,455

[45] Date of Patent: Oct. 25, 1988

[54] LIPOPHILIC COMPLEXES OF PHARMACOLOGICALLY ACTIVE ORGANIC COMPOUNDS

[75] Inventors: Seymour Lieberman, Flushing; V. V. K. Prasad, New York, both of N.Y.; Laura Ponticorvo, Cliffside Park, N.J.

[73] Assignee: The Trustees of Columbia University in the City of New York, New York, N.Y.

[21] Appl. No.: 722,735

[22] Filed: Apr. 12, 1985

[51] Int. Cl.$^4$ .................. A61K 31/685; A61K 31/56; C07J 9/00

[52] U.S. Cl. .................. 514/77; 260/397.2; 514/78; 514/169; 514/170; 514/182

[58] Field of Search .................. 424/83; 514/169, 170, 514/182, 77, 78; 260/397.2

[56] References Cited

U.S. PATENT DOCUMENTS

| | | | |
|---|---|---|---|
| 3,919,430 | 11/1975 | Siegel | 514/169 |
| 3,934,013 | 1/1976 | Poulsen | 514/170 |
| 4,248,867 | 2/1981 | Ikushima et al. | 260/397.2 |

OTHER PUBLICATIONS

Grimellec, et al. Lipids 19(6) 474–477 (1984).
Burstein et al. J. Biol. Abst. 238(5) 1656–1660 (1963).
Burstein Biochim. Biophys. Acta 62:576–578 (1962).

*Primary Examiner*—Douglas W. Robinson
*Attorney, Agent, or Firm*—John P. White

[57] ABSTRACT

The present invention provides a composition with the structure $$(L)_m(E)_n$$

wherein m and n are each integers, and m and n are different or the same; L is an ampholytic lipid or polymer, or a nonampholytic lipid with hydrophobic properties; E is a nonlipophilic ionic inorganic ester of an organic compound, E having the structural formula $$Z^{+q}R\text{-}Y\text{-}X\text{-}(O)_p{}^{-q}$$

wherein R is an organic moiety; Y is oxygen, sulfur or a substituted nitrogen, X is sulfur, phosphorus, nitrogen or boron; p is the integer 2 or the integer 3; Z is hydrogen or a metal, and Q is an integer indicating the elecrical charge.

Suitable ampholytic lipids are phospholipids, sulfatides, and sphingomyelins. The esters can be sulfate or phosphate esters of steroid hormones. The compositions are useful for example, for altering the solubility properties of the esters, and for developing controlled-delivery systems for pharmaceuticals.

6 Claims, No Drawings

LIPOPHILIC COMPLEXES OF PHARMACOLOGICALLY ACTIVE ORGANIC COMPOUNDS

BACKGROUND OF THE INVENTION

The present invention relates to novel compositions of non-lipophilic ionic inorganic esters of organic compounds. The inventive compositions are useful, for example, for altering the solubility properties of the esters and for providing controlled-delivery systems for pharmaceuticals.

Frequently a physical property of a chemical must be altered to enable its purification or chemical manipulation. This is often accomplished by chemically modifying a functional group on the molecule. For example, an organic acid may be esterified to render it lipid-soluble, or volatile. A primary difficulty with such chemical modifications of biologically important compounds, such as pharmaceuticals, is that the functional group sought to be altered is often involved in the particular compound's biological activity. Thus, changing the compound's structure can destroy its essential biological activity. Accordingly, the search for methods of altering the physical properties of compounds of interest without altering the chemical structure of the compounds is the subject of active and ongoing research.

Such methods for solubilizing lipophilic compounds in water are known. One of these is the creation of dispersible lipid vesicles or micelles into which lipophilic compounds of interest can be incorporated. For example, Steffan, U.S. Pat. No. 4,158,707 discloses the use of micelles comprising cholic acid and certain lipoids as aqueous vehicles suitable for parenteral administration of medicaments which are insoluble in water. These methods require the careful creation of suitable micelles, detailed knowledge of the extent to which the medicament can be incorporated into the micelles and the physical separation of micelles from the unincorporated material.

Certain limited methods for creating lipophilic complexes of non-lipophilic materials also are available. Thus, lipophilic crown ether complexes of metal ions are known, but crown ether complexes of larger, organic molecules do not exist. Development of lipophilic complexes of such non-lipophilic compounds would be highly desirable, and is an object of the present invention.

A further object of this invention relates to the controlled administration of pharmaceuticals, which is often necessary to insure their maximum effectiveness with a minimum of side effects. The concentration of a drug at the target site may be manipulated by many controlled release means, as described in Benson et al., (1982), Pharmaceuticals, Controlled Release, *Encyclopedia of Chemical Technology* 17, pp. 290–310. Some of these means maintain the concentration of a drug in the bloodstream at a constant level, while others serve to release the drug only to certain organs or tissues. The methods include, for example, delivery modules from which the drug is slowly leached, intravenous drip systems, complex mini-pumping systems placed within the body, and liposome delivery systems. The particular system chosen for delivery of a given pharmaceutical depends upon many factors including the specificity or generality of the drug's site of action, the concentration needed for therapeutic effectiveness, the precision with which a given concentration of the drug must be maintained, and the length of time the optimal dose level must persist. Also important are properties of the pharmaceutical itself as its solubility properties and its stability once released into the bloodstream or tissue. Clearly, modification of the properties of a pharmaceutically effective compound so that it can be administered by a wider range of controlled delivery systems would greatly increase the therapeutic usefulness of the drug.

The present invention provides novel compositions of an ampholytic lipid or polymer, or a suitable non-ampholytic lipid, with a non-lipophilic ionic ester of an organic compound, and methods for making these compositions.

The present invention also provides a composition of a non-lipophilic ionic inorganic ester of an organic compound, the compound having solubility properties which differ from the solubility properties of the ester.

Another embodiment of the present invention provides pharmaceutically effective compositions comprising the novel compounds of interest. The compositions are suitable for controlled delivery of the compounds in a pharmaceutically effective manner.

SUMMARY OF THE INVENTION

The present invention provides a composition with the structure $$(L)_m(E)_n$$

wherein m and n are each integers, and m and n are different or the same; L is an ampholytic lipid or polymer, or a suitable non-ampholytic lipid with hydrophobic properties, E is a non-lipophilic ionic inorganic ester of an organic compound, E having the structural formula $$Z^{+q}R-Y-X-(O)_p^{-q}$$

wherein R is an organic moiety; Y is oxygen, sulfur, or a substituted nitrogen; X is sulfur phosphorus, nitrogen or boron; p is the integer 2 or the integer 3; q is an integer indicating electrical charge; and Z is Hydrogen or a metal.

In the inventive compositions, the values of m and n are variable and depend upon the manner in which the compositions are made.

The component referred to as "L" can be any ampholytic lipid or polymer, such as sphingomyelins, cardiolipins, sulfatides, phospholipids and cellulose and polystyrene which are substituted with ampholytic groups. L can also be a non-ampholytic lipid or polymer, such as distearin, tristearin, and a cellulose or polystyrene substituted with pendant hydrocarbon groups having hydrophobic properties.

The component of the inventive composition referred to as "E" is a non-lipophilic ionic inorganic ester of an organic compound. Preferred esters are phosphates, phosphonates, borates, nitrates and sulfates. Typical esters are derivatives of organic molecules containing hydroxyl, sulfhydryl or amino groups, such as phenols, mercaptans, anilines, terpenes and steroids. Preferred steroids are for example, cholesterol, cholestyramine, progesterone, substituted progesterone, testosterone, substituted testosterone, pregnenolone, substituted pregnenolone, dehydroepiandrosterone, substituted dehydroepiandrosterone, corticoids and aldosterone.

The present invention also provides methods for preparing the inventive compositions which comprise contacting the components in the presence of a solvent. The components, once contacted, spontaneously combine into the inventive compositions.

It is within the scope of the present invention to use the formation of the inventive compositions in order to extract a non-lipophilic ionic inorganic ester of an organic compound into a lipophilic phase, e.g. method of purifying the ester from other hydrophilic substances or to maintain the ester in a lipophilic phase for storage or other purposes.

A further object of the present invention is to provide compositions, including pharmaceutically acceptable compositions, containing inventive compositions which are pharmaceutically effective. These compositions may be in the form of any of the wide variety of pharmaceutically effective compositions known to the pharmaceutical industry, including pastes, solids, liquids, oily suspensions, powders, pills and capsules. These compositions may contain pharmaceutically acceptable carrier materials or other adjuvants and additives known to the art.

Particularly useful pharmaceutical compositions containing the inventive compositions are compositions from which the pharmaceutically active compound is released in a controlled manner. Especially suitable are compositions which contain a hydrophilic substance within a lipophilic phase, and slowly release the substance to the aqueous environment or to the lipophilic regions of target tissue. The nonhydrophobic component of the inventive composition may be released from the controlled-release compositions or both components may be released as a complex. It is also within the scope of this invention for the compositions to contain more than one pharmaceutically active substance in compositions of the instant invention. These substances may be released sequentially, or simultaneously, or simultaneously at different rates, according to the overall pharmacological program.

The controlled-release compositions of the instant inventions are particularly suitable for the creation of contraceptive compositions from which compounds with contraceptive effect are released over a period of time.

DETAILED DESCRIPTION OF THE INVENTION

The present invention provides a composition with the structure

$$(L)_m(E)_n$$

wherein m and n are each integers, and m and n are different or the same; L is an ampholytic lipid or polymer, or L may also be a non-ampholytic lipid with hydrophobic properties; E is a non-lipophilic ionic inorganic ester of an organic compound, E having the structural formula

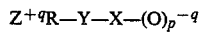
$$Z^{+q}R-Y-X-(O)_p^{-q}$$

wherein R is an organic moiety; Y is oxygen, sulfur or a substituted nitrogen; X is sulfur, phosphorus, nitrogen or boron; p is the integer 2 or the integer 3; q is an integer indicating electrical charge; Z is Hydrogen or a metal.

In the inventive compositions, the values of m and n are variable and depend upon the manner in which the compositions are made. Factors likely to influence the values of m and n are the solvents used to dissolve the compound, the precise chemical structures of L and E, and the concentration of the compound. Thus, the values of m and n can vary from about 1 and about one million or more. The ratio of m and n range from about 0.01 to about 100. The ratio of m and n is typically between about 0.1 and about 10, e.g. about 1. It is entirely possible that a composition of this invention will comprise a mixture of complexes of differing overall sizes and differing ratios of m and n.

The component of the inventive compositions referred to as "L" can be any ampholytic lipid or polymer. Suitable examples of ampholytic lipids are sphingomyelins, sulfatides, and phospholipids such as dipalmitoyl phosphatidylethanolamine, dipalmitoyl phosphatidylcholine, dipalmitoyl phosphatidylserine and 3'-O-lysylphosphatidylglycerol. Suitable ampholytic polymers are cellulose and polystyrene which are substituted with ampholytic groups such as, for example, amino acids. Suitable non-ampholytic lipids are diacyl-andd triacyl-glycerols, cardiolipins and diacylphosphatidyl inositol.

The component of the inventive composition referred to as "E" is a non-lipophilic ionic inorganic ester of an organic compound. Preferred esters are phosphates, phosphonates, borate, nitrates and sulfates. Typical esters are derivatives of organic molecules such as cyclohexanol, phenol, terpenes, and steroids. Preferred steroids are for example, cholesterol, substituted cholesterol, progesterone, substituted progesterone, testosterone, substituted testosterone, pregnenolone, substituted pregnenolone, dehydroepinandiosterone, and substituted dehydroepiandrosterone and corticoids. The only known limitation on the structure of the organic compounds which can be incorporated into the inventive complexes is that they must be esterifiable with a phosphate, sulfate, borate, nitrate or phosphonate group. Many methods are known to those of ordinary skill in the art of structurally altering the compounds disclosed above without altering the essential function of the compounds; this invention is therefore broadly directed to complexes of non-lipophilic ionic inorganic acid esters of organic compounds, and is not intended to be limited to the particular compounds disclosed above.

The manner of bonding between "L" and "Z" is not known with particularity but it is not covalent in the usual usage of the work. "Z" represents a hydrogen or metal cation of charge +q present in sufficient quantity to render the complex neutral with respect to overall charge. Preferred cations are $NH_4^+$, $NR_4^+$, $Na^+$, $K^+$, $Mg^{2+}$, and $Mn^{2+}$. Cations which are particularly preferred due to their low cost and easy availability are $K^+$ and $Na^+$.

The solubility properties of the inventive compositions are dependent upon the nature of the substituent components. For example, a composition of cholesterol sulfate and phosphatidylethanolamine is very lipophilic and will partition into hexane from aqueous methanol solution. However a composition of cholesterol sulfate and dipalmitoyl phosphatidylcholine is less lipophilic and will partition into hexane from water, but it will partition less easily from a methanol: water (4:1, v:v) mixture.

These solubility properties are used to determine the partition coefficients or ratios which are derived as shown in the Examples below. For example, a composition of cholesterol sulfate with lecithin, cephalin or cardiolipin will be extracted entirely into benzene from a water solution or suspension. On the other hand, a composition of cholesterol sulfate and di- or tri-stearin partitions almost equally between the two phases.

The present invention also provides methods for preparing the inventive compositions which comprise contacting the components in the presence of a solvent. The components, once contacted, spontaneously combine into the inventive compounds. Thus, there are many means known to those of ordinary skill in the art for accomplishing complex formation according to this invention. For example, the components may be dispersed into the same solvent, or dispersed into separate solvents which are then contacted. When separate solvents are used, they may be miscible or immiscible. Once the complex has formed, the solvents may be separated if they are immiscible, or evaporated off, and replaced with a different solvent. It is therefore within the scope of the present invention to crease a substantially solvent-free preparation of the inventive composition which can then be solubilized as needed.

Many factors can affect the extent and type of composition formed such as, for example, the types of solvents used, the salt concentration, pH, temperature, and time for which the components are mixed.

The composition of dipalmitoyl phosphatidylethanolamine and cholesterol sulfate will serve to illustrate some of these principles. The composition can be formed by mixing together a solution of cholesterol sulfate in a hydrophilic solvent such as water or water/methanol with a solution of dipalmitoyl phosphatidylcholine in an organic solvent such as hexane, isooctane, benzene, chloroform, or other suitable organic solvents. The composition partitions into the organic phase. The aqueous or aqueous-methanol solvent can be removed, and the organic solvent dried off leaving a dry preparation of the composition. Alternatively, the cholesterol sulfate may be dispersed in a chloroform solution containing phospholipid, and the chloroform then dried off.

It is within the scope of the present invention to use the formation of the inventive compositions in order to extract a non-lipophilic ionic inorganic ester of an organic compound into a lipophilic phase. This may be done, for example, as a prelude to performing an organic solvent-based reaction on the ionic ester, as a method of purifying the ester from other hydrophilic substances; or simply to maintain the ester in a lipophilic phase for storage or other purposes. Manipulation of the salt content or pH of the aqueous phase can disrupt the composition and cause the ester to become hydrophilic and return to the aqueous phase. For example, addition of sodium hydroxide to the aqueous phase will disrupt the lipophilic complex of cholesterol sulfate and dipalmitoyl phosphatidylethanolamine, and cause the cholesterol sulfate to partition back into the aqueous phase.

A further object of the present invention is to provide compositions including pharmaceutically acceptable compositions containing inventive compositions which are pharmaceutically effective. These pharmaceutical compositions may be in the form of any of the wide variety of pharmaceutically effective compositions known to the pharmaceutical industry, including pastes, solids, liquids, oily suspensions, powders, pills and capsules. These compositions may contain pharmaceutically acceptable carrier materials such as, for example, starch, gelatin, agar, sugar, carboxymethylcellulose, polyvinylalcohol, magnesium stearate, and sodium alginate. In addition, these preparations may contain other adjuvants and additives known to the art. These compositions may be administered by various means such as subcutaneous pellet or paste, or as an injectible oily suspension.

It is within the scope of this invention to provide compositions suitable for use in animals, humans, bacteria and plants.

Particularly useful pharmaceutical compositions containing the inventive compounds are compositions from which the compound is released in a controlled manner. Many such controlled-release pharmaceutical compositions are known to the art, and the present invention is broadly capable of being used in such controlled-release compositions. Especially suitable are compositions which contain a lipophilic substance within a lipophilic phase, and slowly release the substance to the aqueous environment or to the lipophilic regions of target tissue. Note that the nonhydroscopic component of the inventive compound may be released from the controlled-release compositions or both components may be released as a complex. It is also within the scope of this invention for the compositions to contain more than one pharmaceutically active substance in compounds of the instant invention. These substances may be released sequentially, or simultaneously, or simultaneously at different rates, according to the overall pharmacological program.

The controlled-release pharmaceutical compositions of the instant inventions are particularly suitable for the creation of contraceptive compositions from which compounds with contraceptive effect are released over a period of time. This period of time can be from about one day to about several years. The time period is typically about one month, but can also be for periods of several months or years.

The present invention also concerns methods of applying pharmaceutically active materials such as contraceptives which comprises applying a suitable amount of the pharmaceutical compositions to the the body. The composition can be applied directly on the target tissue or on some other accessible area of the body. The methods apply to humans and also to animal patients or subjects.

This invention is illustrated in the examples which follow.

The examples are set forth to aid in understanding of the invention but are not intended to, and should not be construed to limit in any way the invention as set forth in the claims which follow thereafter.

EXAMPLE I

Preparation of Cholesterol Sulfate

Cholesterol sulfate is available commercially or may be prepared as follows.

Cholesterol and sulfurtrioxide-pyridine complex were mixed. To the mixture, NaOH or KOH was then added. The mixture is then poured into on aqueous solution of sodium or potassium carbonate and lyophilized to yield the sodium or potassium salts, respectively.

EXAMPLE II

Preparation of a lipophilic complex of cholesterol sulfate

One equivalent of cholesterol sulfate was dissolved in methanol-water (9:1, v:v) and extracted with isooctane. Greater than 94% of the sulfate remained in the methanol-water phase. The isooctane layer (upper layer)

was discarded. Then one equivalent of phosphatidylethanolamine dissolved in isooctane was added to the sulfate-containing methanol-water preparation. After shaking (to mix the two phases) over 90% of the sulfate was found in the isooctane layer. The isooctane layer was removed, and the isooctane was dried off. The remaining dry material exhibited in the infrared spectrum absorptions characteristic of cholesterol sulfate (about 1220 cm.$^{-1}$), the acyl carbonyls (about 1730 cm.$^{-1}$) and NH stretches (about 3300 cm.$^{-1}$) of the phospholipid.

EXAMPLE III

Preparation of lipophilic complex of cholesterol sulfate

Cholesterol sulfate is dissolved in chloroform or methanol. To this mixture is added chloroform containing phosphatidylethanolamine. The solvent is then evaporated, and the dry residue solubilized in a nonpolar solvent.

EXAMPLE IV

Solubilization of sodium Cholesterol Sulfate by an equimolar amount of an additive Tritiated sodium cholesterol sulfate was prepared from tritiated cholesterol (New England Nuclear) by organic synthesis methods known to those of ordinary skill in the art.

A solution of 50 μg of the tritiated sodium cholesterol sulfate in 100 μl methanol was prepared. To aliquots of this solution was added a warm CHCl$_3$ solution of each of the additives listed in Table I. The CHCl$_3$ solution of the additives contained an equivalent molar amount of the additive relative to the amount of cholesterol sulfate. After addition of the additive solution the mixture was taken to dryness under nitrogen. 1.5 ml of benzene were added and warmed at 65° C. for ten seconds in a water bath. An aliquot (100 λ) was immediately taken and analyzed by counting the signal emitted from the tritum in a radioactive scintillation counter.

TABLE I

| Additives | Molecular Weight g/mole | Amount Added in μg | Relative[a] Efficiency | Partition Ratio (Value) Max = 1 in 1.5 ml C$_6$H$_6$ 1.5 ml H$_2$O |
|---|---|---|---|---|
| | | | 0.0 | |
| Lecithin (Dipalmitoylphosphatidylcholine) | 734 | 73 | 0.88 | 0.98 |
| Cephalin (dipalmitoylphosphatidylethanolamine) | 692 | 70 | 0.9 | 0.95 |
| 1,2-dipalmitoyl racemic glycerol | 569 | 56 | 0.02 | 0.30 |
| Cardiolipin | 1200 | 120 | 1.0 | 0.92 |
| Tristearin | 890 | 90 | .01 | 0.50 |

[a]Relative Efficiency is defined as the amount of sterol sulfate solubilized in the lipid phase by the additive relative to the amount solubilized in the lipid phase by the additive cardiolipin. The amount solubilized by the cardiolipin itself is greater than 95% of the maximum.

To determine the partition coefficient a warm benzene solution of the complex (e.g. 1.5 ml) was briefly warmed for approximately 10 seconds in a water bath maintained at 65° C. An equivalent volume of water (e.g. 1.5 ml) warmed to 65° C. was then added and the mixture was shaken. The mixture was then placed in a water bath maintained at approximately 65° C. for approximately 1 minute or until the mixture separated into organic and aqueous layers. Aliquots from both the organic and aqueous layers were taken for analysis, and counted on a scintillation counter.

Results

The lecithin, cephalin and cardiolipin complexes of cholesterol sulfate are lipophilic. The 1,2 dipalmitoyl racemic glycerol and the tristearin complexes with cholesterol sulfate formed in the presence of water also displayed lipophilicity whereas the sodium cholesterol sulfate is insoluble when mixed with 1,2 palmitoyl racemic glycerol or tristearin in an organic solvent. While not wishing to be bound by theory, this effect may be due to a restructuring of the molecular aggregates of the additives in the presence of water such that they create a strong enough hydrophobic core for the steroid nucleus to interact with, which counters the hydrophilicity of the sulfate group.

EXAMPLE V

Comparison of the Partition Ratios of Sodium Cholesterol sulfate complexes, and cholesterol complexes with Different Additives Mixtures of each of the complexes in benzene and water are formed as described above. The mixtures were warmed at 65° C. and shaken as described previously. Aliquots from the organic and aqueous layers were taken and analyzed by detecting the signal emitted from the tritium in a liquid scintillation counter. The results of the comparison of partion ratios are listed in Table II.

TABLE II

| | Partition Ratio[a] Max = 1 | |
|---|---|---|
| Additive | Sodium Cholesterol Sulfate | Cholesterol |
| Lecithin | 0.98 | 0.85 |
| Chephalin | 0.95 | 0.85 |
| 1,2 dipalmitoyl racemic glycerol | 0.30 | 1.0 |
| Cardiolipin | 0.92 | 0.98 |
| Tristearin | 0.50 | 1.0 |

(a) $\frac{\text{cpm in upper phase}}{\text{cpm in upper phase + cpm in lower phase}}$;
cpm = counts per minute

EXAMPLE VI

Experiments to test time delayed metabolic clearance rate of steroid sulfate-phospholipid complex Pairs of rats (Wistar) were injected subcutaneously with uncomplexed ($^3$H)-dehydroandrosterone sodium sulfate and with a 1:1 phospholipid (dipalmitoylphosphatidylethanolamine) complex of the steroid sulfate. As a control, a 1:1 complex of the phospholipid and underivatized steroid, dehydroandrosterone (DHA)

was also administered to a fifth rat. Feces and urine were collected at 24h, 48h and 120h. Excreta at each time period were combined with 200 ml of methanol and blended for 30 seconds. The methanol extracts were filtered and aliquots counted for radioactivity.

Results: The underivatized steroid (DHA)-phospholipid mixture at all measured intervals showed a metabolic clearance rate that was twice as fast as that of the uncomplexed steroid sodium sulfate. Initially (24h) no significant difference between the uncomplexed and complexed sulfate salts was observed. At the latter two time points (48h, 120h), however, the phospholipid complex of the steroid sodium sulfate was metabolically cleared at a rate 25-30% slower than the uncomplexed steroid sulfate.

What is claimed is:

1. A lipophilic composition having the formula:

$$(L)_m(E)_n$$

wherein $(L)_m$ and $(E)_n$ are bound as a complex, wherein L is selected from the group consisting of phospholipids, cardiolipins, distearins and tristearins; wherein E is cholesterol sulfate or sodium cholesterol sulfate; and wherein m and n are each integers which may be the same or different.

2. A composition according to claim 1, wherein the phospholipid is phosphatidylethanolamine.

3. A method of forming the complex of claim 1, comprising contacting the L and the E in the presence of a solvent.

4. A method according to claim 3, wherein the lipophilic phase comprises the solvent isooctane, benzene, chloroform, or hexane.

5. A pharmaceutical complex comprising at least one composition according to claim 1 in combination with at least one pharmacologically acceptable excepient, the preparation being a preparation in the form of a solid, paste, liquid, oily suspension, powder, pill, or capsule.

6. The pharmaceutical composition according to claim 5, wherein the composition is a sustained release dosage form.

* * * * *